United States Patent [19]

Rivlin

[11] Patent Number: 5,698,227
[45] Date of Patent: Dec. 16, 1997

[54] COMPOSITIONS COMPRISING LIDOCAINE AND EMU OIL AND METHODS OF USE THEREOF

[76] Inventor: Daniel Rivlin, 4000 Towerside Ter. #2303, Miami, Fla. 33138

[21] Appl. No.: 685,307

[22] Filed: Jul. 23, 1996

[51] Int. Cl.⁶ .................................................. A61K 35/12
[52] U.S. Cl. ......................................... 424/522; 514/626
[58] Field of Search ............................ 424/522; 514/626

[56] References Cited

U.S. PATENT DOCUMENTS

| | | | |
|---|---|---|---|
| 5,431,924 | 7/1995 | Ghosh et al. | 424/522 |
| 5,472,713 | 12/1995 | Fein et al. | 425/522 |

OTHER PUBLICATIONS

American Emu Association News, vol. 5, No. 1, Jan./Feb. 1995 at 1.
American Emu Association News, vol. 5, No. 2, Mar. 1995 at 1.
Emu Today and Tomorrow, Oct., 1994 at 15.
Emu Today and Tomorrow, Nov. 1994.
Emu Today and Tomorrow, Jul. 1995 at 27.
Emu Today and Tomorrow, Jul. 1995 at 84.
Longevity, Sep. 1995.

*Primary Examiner*—Jean C. Witz
*Attorney, Agent, or Firm*—Brumbaugh, Graves, Donohue & Raymond

[57] ABSTRACT

The present invention provides compositions comprising lidocaine and emu oil. The compositions are useful in a method of anesthetizing cornified skin comprising topically administering the subject compositions. The present compositions and methods permit rapid and effective anesthesia of cornified skin, such that various surgeries and interventions can be performed without the need for subcutaneous injections of local anesthetics. The present invention further provides a compartmentalized kit having a first container providing emu oil and a second container providing an aqueous solution of lidocaine.

23 Claims, No Drawings

COMPOSITIONS COMPRISING LIDOCAINE AND EMU OIL AND METHODS OF USE THEREOF

FIELD OF THE INVENTION

Various anesthetics, including lidocaine, are effective as topical anesthetics for mucuous membranes and as very superficial anesthetics for the skin. Injections are generally required for anesthesia of cornified skin. The present invention provides a topical anesthetic preparation that rapidly penetrates the large stratum corneum, and thus allows effective topical anesthesia for cornified skin. The present compositions contain lidocaine and emu oil.

BACKGROUND OF THE INVENTION

Lidocaine is a widely used local anesthetic administered by injection or topical administration. Available preparations for topical administration include creams, ointments, jellies, solutions and aerosols. Direct topical application is used for anesthesia of mucous membranes of the nose, mouth, throat, tracheobronchial tree, esophagus and genitourinary tract. Anesthesia following topical administration is completely superficial and does not extend to submucosal structures.

Topical anesthetics intended for use on cornified skin suffer from significant deficiencies. In particular, preparations of lidocaine intended for use on normal skin generally provide only very superficial anesthesia and/or require very long application. For example, EMLA® cream, an emulsion of lidocaine and prilocaine, is reportedly indicated as a topical anesthetic for use on normal intact skin, but requires application for at least one hour to acheve anesthesia suitable for minor dermal procedures. Accordingly, local anesthesia of cornified skin generally requires painful and inconvenient subcutaneous injections.

In accordance with the present invention it has been discovered that a preparation containing emu oil and lidocaine yields significant topical anesthesia in a relatively short amount of time. Emu oil is extracted or rendered from the subcutaneous fat of the back of the emu, a native Australian bird that is a member of the ratite family of flightless birds. Emus are bred commercially in North America and Australia. The extracted oil, which is commercially available, contains triglyceride esters of long chain fatty acids including oleic, linoleic, palmitic and stearic acids.

The Aboriginal peoples of Australia have reportedly used emu oil for centuries for the treatment of skin conditions and muscle and joint pain. More recently, emu oil has been reported to have a variety of uses, including treatment of bruised, burned and dry skin tissue, and as a moisturizer in cosmetic preparations. U.S. Pat. No. 5,472,713 discloses a variety of uses for emu oil, including lowering cholesterol, trigylceride and low density lipoproteins, increasing high density lipoproteins, and improving growth and condition of nails. Topical application of emu oil is disclosed for treatment and prevention of allergies, nosebleeds, headaches and scarring. U.S. Pat. No. 5,431,924 discloses an anti-inflammatory composition containing an emu oil component. The '924 patent discloses that emu oil exhibits dermal absorption, but that a transport enhancer such as isopropyl alcohol or eucalyptus oil is necessary to achieve anti-inflammatory effect by topical administration. An emu trade association publication (*Emu Today and Tomorrow*, October 1994, at 15) reports that the oil is penetrating, emulsifying, non-comedogenic and non-irritating, and further that a product containing emu oil and alpha-hydroxy acid is under development.

Emu oil is commercially available as the purified oil, and in creams, lotions and soaps for moisturizers, cosmetics, and preparations for temporary relief of muscle and joint pain. However, very little conclusive documented research concerning the use of emu oil has been reported. A composition comprising emu oil, methyl ethyl salicylate, isopropyl salicylate and oil of eucalyptus reportedly exhibits anti-inflammatory and anti-arthritic activity in a laboratory rat polyarthritis model (*American Emu Association News* March 1995 at 1,5). Clinical studies to determine the effect of emu oil on arthritis of the hands (*Emu Today and Tomorrow*, July 1995, at 84) and healing of burn wounds (*American Emu Association News* January/February 1995 at 1,5) have been proposed. The reported anti-inflammatory properties of emu oil have led to speculation that it may act as a transdermal carrier, but this use remains speculative (*American Emu Association News* March 1995 at 1,5).

Accordingly, there is a need in the art for a topical anesthetic capable of effectively penetrating the stratum corneum. It has been discovered in accordance with the present invention that a composition comprising lidocaine and emu oil can achieve anesthesia of cornified skin when applied topically.

SUMMARY OF THE INVENTION

The present invention is directed to compositions comprising lidocaine and an effective amount of emu oil to achieve anesthesia of cornified skin by topical application.

The present invention further provides a method of anesthetizing cornified skin comprising topically administering a composition comprising lidocaine and an effective amount of emu oil.

The present invention further provides a compartmentalized kit having a first container containing emu oil and a second container containing an aqueous solution of lidocaine.

In another embodiment, the present invention provides an article of manufacture comprising a packaging material and a pharmaceutical composition contained within the packaging material, wherein the pharmaceutical composition comprises emu oil and lidocaine, and wherein the packaging material comprises a label that indicates that the composition can be used for topical anesthesia of cornified skin.

DETAILED DESCRIPTION OF THE INVENTION

The present invention provides compositions for topical anesthesia of cornified skin wherein the compositions comprise lidocaine and emu oil. In another embodiment, the compositions consist essentially of emu oil and lidocaine. Cornified skin is also referred to herein as normal skin. Lidocaine as used herein refers to acetamide, 2-(diethylamino)-N(2,6-dimethylphenyl) and the monohydrochloride form known as lidocaine HCl or xylocaine.

It has been discovered in accordance with the present invention that compositions containing lidocaine and an effective amount of emu oil provide anesthesia of cornified skin when applied topically. An effective amount of emu oil is defined as that amount which, when combined with lidocaine, provides anesthesia of skin commencing within from about ten to about thirty minutes from topical application.

Lidocaine is a well known and commercially available local anesthetic. For the compositions of the present invention, lidocaine is preferably used in aqueous solution at a concentration generally used in the art for local anesthesia. Market preparations of 0.5% to 5% are available and are suitable for use in the present invention. In a preferred embodiment, a 1% lidocaine aqueous solution is used to prepare the present compositions.

Lidocaine is known to be effective as an anesthetic with and without a vasoconstrictor. However, vasoconstrictors are added to some market preparations to decrease toxicity and prolong duration of action. For example, lidocaine is available as solutions with epinephrine at 1:10,000 to 1:200,000 dilution. Such solutions of lidocaine with epinephrine are also suitable for use in preparation of the present compositions. In a preferred embodiment, an aqueous solution of 1% lidocaine with 1:10,000 epinephrine is used in the present compositions.

Emu oil is extracted or rendered from the subcutaneous fat of the back of the emu, *Dromideius novaehollandiae* as described for example in U.S. Pat. No. 5,472,713, the disclosure of which is incorporated herein by reference. Briefly, the emu is processed to obtain the subcutaneous layer of fat, and the fat is rendered by methods known in the art to obtain the oil. Emu oil obtained by this method is yellow and has an odor. The oil may be further refined to remove the yellow component and to reduce odor. Methods for removing the yellow component may be found in U.S. Pat. No. 5,431,924, the disclosure of which is incorporated herein by reference. In accordance with the present invention, emu oil may be used with or without the yellow component. The oil contains triglyceride esters of long chain fatty acids including oleic, linoleic, palmitic and stearic acids. Details of the fatty acid content of emu oil are disclosed in U.S. Pat. Nos. 5,431,924 and 5,472,713. Emu oil is also available from commercial sources including Planet Emu, 1521 Alton Road #187, Miami, Beach, Flor. and New World Technology, Inc., P.O. Box 7580, Greenwich, Conn.

The compositions of the present invention contain an effective amount of emu oil in combination with lidocaine. In a preferred embodiment, the compositions comprise emu oil and lidocaine in a ratio of at least 1:1 by volume and preferably in a ratio of at least 2:1. In a more preferred embodiment the ratio of emu oil to lidocaine is from about 2:1 to about 3:1. The ordinarily skilled artisan can optimize the ratio of emu oil to lidocaine in accordance with the teachings herein. Optimization may be necessary since the composition of emu oil may vary slightly from batch to batch, for example in fatty acid content, due to variations in the purification process, age and storage conditions of the oil, diet and environment of the emu, and so on.

The ordinarily skilled artisan can determine an effective amount of emu oil for use in the subject compositions by the following assay. Emu oil is combined in varying ratios with an aqueous solution of 0.5% to 5% lidocaine. Preferably 1% lidocaine is used. The preparation is shaken vigorously and applied topically to a site on the forearm of a human subject. After ten minutes, the site is challenged with a pin prick of a thirty gauge needle. An amount of emu oil that, in combination with 1% lidocaine, provides complete anesthesia to the pin prick is considered to be effective amount of emu oil.

The compositions of the present invention are prepared by combining an effective amount of emu oil with an aqueous solution of lidocaine and vigorously shaking the resulting emulsion. The aqueous solution of lidocaine is a 0.5% to 5% solution. In a preferred embodiment, an aqueous 1% solution of lidocaine is used. In another preferred embodiment, an aqueous solution of 1% lidocaine with 1:10,000 epinephrine is used in the present compositions. The solutions are prepared by combining emu oil and the aqueous lidocaine solution at a ratio of at least 1:1 by volume, i.e. by using a greater volume of emu oil per volume of lidocaine solution. In a preferred embodiment, the ratio of emu oil to lidocaine is from about 2:1 to about 3:1. In other words, two to three volumes of emu oil are used per volume of lidocaine solution. The compositions may further contain pharmaceutically acceptable carriers and/or diluents, including for example solvents, dispersion media, antibacterial agents, antifungal agents, and so on that are not incompatible with the active ingredients.

The present invention further provides a method of anesthetizing cornified skin comprising topically administering a composition comprising lidocaine and an effective amount of emu oil to cornified skin of a subject. In a preferred embodiment, the composition comprises a ratio of emu oil to 1% aqueous lidocaine solution of from about 2:1 to about 3:1. The compositions of the invention are applied topically to a desired site on cornified skin of a human subject, and may be allowed to dry or may be covered with a dressing. After ten to thirty minutes, the compositions provide topical anesthesia through transdermal absorption. The skilled artisan can determine the appropriate volume of the compositions to apply to achieve the desired effect. For example, about 0.25 ml of the composition may be applied over a site on cornified skin having a surface area of about 1 cm$^2$. The anesthesia that is achieved by the present method is suitable for dermal procedures that generally require subcutaneous injection of lidocaine, including for example, punch biopsy.

The present invention further provides a compartmentalized kit having a first container containing emu oil and a second container containing an aqueous solution of lidocaine. In a preferred embodiment the aqueous solution of lidocaine is 0.5% to 5% lidocaine, and more preferably 1% lidocaine. In another embodiment, the aqueous solution of lidocaine further contains epinephrine at a dilution of from 1:10,000 to 1:200,000. The kits of the present invention allow the extemporaneous preparation of the present compositions for use as a topical anesthetic for cornified skin.

The present invention further provides an article of manufacture comprising a packaging material and a pharmaceutical composition contained within the packaging material, wherein the pharmaceutical composition comprises emu oil and lidocaine, and wherein the packaging material comprises a label that indicates that the composition can be used for topical anesthesia of cornified skin. The pharmaceutical compostions may be prepared as described hereinabove. The packaging material can comprise glass, plastic, metal, or any other suitable inert material that does not react with any of the ingredients contained therein.

The invention is further illustrated by the following specific example which is not intended in any way to limit the scope of the invention.

EXAMPLE 1

Emu oil with the yellow component obtained from Emu Man, P.O. Box 745, Claremont, West Australia was mixed in a 1:1 ratio, a 2:1 ratio or a 3:1 ratio with 1% lidocaine with 1:10,000 epinephrine. The emulsion was shaken vigorously. Immediately after shaking, the emulsion was topically applied to the forearm of a subject in two locations. Two subjects received the 1:1 ratio, four subjects received the 2:1 ratio, and three subjects received the 3:1 ratio. Tegaderm, a hydrocolloid dressing, was applied over one location and the other location was allowed to dry. After ten minutes the sites were challenged with a pin prick of a thirty gauge needle as well as a hyfrecator set at ten watts. A similar site was challenged on the opposite untreated arm.

The two subjects who had the 1:1 ratio applied to their skin reported no difference in pain with either stimulation at any of the tested sites. The remaining seven subjects, four of whom had a 2:1 ratio and three of whom had a 3:1 ratio of emu oil to lidocaine applied to the test site, reported a marked reduction in pain in both the Tegaderm and air dried sites as compared to the untreated site. All four subjects who had the 2:1 ratio applied reported complete anesthesia. Two of the three subjects who had the 3:1 ratio applied reported complete anesthesia. The remaining subject with the 3:1 ratio reported about 80% anesthesia.

This example demonstrates that a combination of emu oil and lidocaine in a 2:1 or 3:1 ratio provides significant topical anesthesia within ten minutes.

I claim:

1. A composition comprising an effective amount of lidocaine and an effective amount of emu oil to achieve anesthesia of cornified skin by topical application.

2. The composition of claim 1 wherein said lidocaine is an aqueous solution of from 0.5% to 5% lidocaine.

3. The composition of claim 1 wherein said lidocaine is an aqueous solution of 1% lidocaine.

4. The composition of claim 1 prepared by combining emu oil and a 1% aqueous solution of lidocaine at a ratio of emu oil to lidocaine, by volume, of 2:1 to 3:1.

5. A method of anesthetizing cornified skin comprising topically administering a composition comprising an effective amount of lidocaine and an effective amount of emu oil to cornified skin of a subject.

6. The method of claim 5 wherein said lidocaine is an aqueous solution of from 0.5% to 5% lidocaine.

7. The method of claim 5 wherein said lidocaine is aa aqueous solution of 1% lidocaine.

8. The method of claim 5 wherein said lidocaine is an aqueous solution of from 0.5% to 5% lidocaine with epinephrine at a 1:10,000 to 1:200,000 dilution.

9. The method of claim 5 wherein said lidocaine is an aqueous solution of 1% lidocaine with epinephrine at a 1:10,000 dilution.

10. The method of claim 5 wherein said emu oil and said lidocaine are present in a ratio, by volume, of from about 1:1 to about 3:1.

11. The method of claim 5 wherein said emu oil and said lidocaine are present in a ratio, by volume of emu oil to lidocaine, of from about 2:1 to about 3:1.

12. The method of claim 5 wherein said emu oil and said lidocaine are present in a ratio, by volume of emu oil to lidocaine, of 2:1.

13. The method of claim 5 wherein said emu oil and said lidocaine are present in a ratio, by volume of emu oil to lidocaine, of 3:1.

14. An article of manufacture comprising a packaging material and a pharmaceutical composition contained within said packaging material, wherein said pharmaceutical composition comprises an effective amount of emu oil and lidocaine, and wherein said packaging material comprises a label that indicates that said composition can be used for topical anesthesia of cornified skin.

15. A composition comprising an effective amount of lidocaine and an effective amount of emu oil to achieve anesthesia of contitled skin by topical administration wherein said lidocaine is an aqueous solution of from 0.5% to 5% lidocaine with epinephrine at a 1:10,000 to 1:200,000 dilution.

16. The composition of claim 15 wherein said lidocaine is an aqueous solution of 1% lidocaine with epinephrine at a 1:10,000 dilution.

17. The composition of claim 15 wherein said emu oil and said lidocaine are present in a ratio, by volume of emu oil to lidocaine, of from about 1:1 to about 3:1.

18. The composition of claim 15 wherein said emu oil and said lidocaine are present in a ratio, by volume of emu oil to lidocaine, of from about 2:1 to about 3:1.

19. The composition of claim 15 wherein said emu oil and said lidocaine are present in a ratio, by volume of emu oil to lidocaine, of 2:1.

20. The composition of claim 15 wherein said emu oil and said lidocaine are present in a ratio, by volume of emu oil to lidoaine, of 3:1.

21. A composition prepared by combining emu oil and lidocaine at a ratio, by volume of emu oil to lidocaine, of from about 1:1 to about 3:1.

22. The composition of claim 21 wherein said lidocaine is an aqueous solution of from 0.5% to 5% lidocaine with epinephrine at a 1:10,000 to 1:200,000 dilution.

23. A method of anesthetizing contitled skin comprising topically administering the composition of claim 15 to cornified skin of a subject.

* * * * *